United States Patent [19]

Curtis-Prior et al.

[11] Patent Number: 4,804,674

[45] Date of Patent: Feb. 14, 1989

[54] VAGINAL PHARMACEUTICAL COMPOSITION

[75] Inventors: Peter B. Curtis-Prior, Histon; Stewart T. Leslie, Cambridge, both of United Kingdom; Ronald B. Miller, Basel, Switzerland; Alison L. Shill, Histon, United Kingdom

[73] Assignee: Euroceltique, S.A., Luxembourg, Luxembourg

[21] Appl. No.: 27,886

[22] Filed: Mar. 19, 1987

[30] Foreign Application Priority Data

Mar. 26, 1986 [GB] United Kingdom ................ 8607570

[51] Int. Cl.$^4$ .................. A61K 31/195; A61K 31/415
[52] U.S. Cl. .................................... 514/400; 514/561; 514/563; 514/565
[58] Field of Search ........ 514/400, 638, 667, 841–843, 514/561, 563, 565; 424/DIG. 14, DIG. 15

[56] References Cited

U.S. PATENT DOCUMENTS 2,918,404  12/1959  Mende et al. ...................... 514/841

OTHER PUBLICATIONS

Barnhart, E. R., Physicians' Desk Reference, 1986, pp. 1282–1283, Medical Economics Company Inc.
Tanabe, CA 96 #187088g (1982).

Primary Examiner—Leonard Schenkman
Attorney, Agent, or Firm—Steinberg & Raskin

[57] ABSTRACT

A vaginal pharmaceutical composition having sperm motility enhancing activity comprising a sperm motility enhancing amount of at least one sperm motility enhancing amino acid or amino acid salt in combination with a vaginally acceptable diluent or carrier.

Preferred active materials are aspartic acid, glutamic acid, arginine, histidine, asparagine, glutamine and arginine aspartate. L-amino acids or salts are particularly preferred.

The preparation may be in the form of a pessary, a cream, a liquid douche, a gel, an aerosol foam or a controlled delivery device.

6 Claims, No Drawings

VAGINAL PHARMACEUTICAL COMPOSITION

The present invention relates to a vaginal pharmaceutical composition having sperm motility enhancing activity and, in particular, to such a composition containing a sperm motility enhancing amino acid.

According to one aspect of the present invention there is provided a vaginal pharmaceutical composition having sperm motility enhancing activing comprising a sperm motility enhancing amount of at least one sperm motility enhancing amino acid or amino acid salt in combination with a vaginally acceptable diluent or carrier.

According to another aspect of the present invention there is provided the use of at least one sperm motility enhancing amino acid or amino acid salt for the manufacture of a vaginal pharmaceutical composition for the enhancement of sperm motility in the vagina of a female mammal, especially a human female.

The at least one sperm motility enhancing amino acid or amino acid salt of this inventon may be any amino acid or salt, that, at a concentration between 1 mM and 25 mM, increases sperm motility by at least 15%, preferably by at least 25%, (of control), using the transmembrane migration method described hereinafter under "Measurement of Human Sperm Motility".

Preferably the at least one amino acid or amino acid salt has an acidic, basic or amide side chain. Preferred amino acids are aspartic acid, glutamic acid, arginine, histidine, asparagine and glutamine, especially arginine and asparagine. A preferred salt is the aspartic acid salt of arginine (arginine aspartate). In a particularly preferred embodiment of the present composition, the amino acid (or salt) is an L-amino acid (or salt).

The present pharmaceutical composition may be in any form suitable for application to the vagina and consistent with its purpose, namely enhancing sperm motility in the vagina. For example, the composition may be in the form of a pessary, a cream, a liquid douche, a gel, an aerosol foam or a controlled delivery device.

The vaginally acceptable diluent or carrier must not inhibit the movement of sperm or have any other undesirable (in particular contraceptive) characteristics.

The amount of the at least one sperm motility enhancing amino acid or amino acid salt in a unit dose of the present pharmaceutical composition must be sufficient to produce a sperm motility enhancing effect in the vagina of a female mammal. In the present specification this means that the amount in a unit dose must be sufficient, when dissolved in a 6.66 ml volume of phosphate buffer saline (pH 7.3), to increase sperm motility by at least 15% preferably by at least 25%, (of control), using the transmembrane migration method described hereinafter under "Measurement of Human Sperm Motility." The 6.66 ml volume of PBS is derived from an assumed vaginal volume of 20 ml.

Generally, this means that the amount (of amino acid/salt in a unit dose) is at least 0.02 mmoles. Preferably a unit dose will contain between 0.02 and 2 mmoles, especially between 0.1 and 1 mmole, of the at least one amino acid/salt. In particularly preferred embodiments of this invention, the composition contains between 3.5 and 350 mg, especially between 17.5 and 175 mg, of L-arginine or between 2.7 and 270 mg, especially between 13.5 and 135 mg, of L-aspartic acid. Preferably a unit dose of the present composition weighs between 0.25 and 5.0 gm.

According to another aspect of the present invention there is provided a process for the preparation of a vaginal pharmaceutical composition having sperm motility enhancing activity comprising combining a predetermined amount of at least one sperm motility enhancing amino acid or amino acid salt with a vaginally acceptable diluent or carrier, the predetermined amount of the at least one amino acid or amino acid salt being such that a unit dose of the composition contains a sperm motility enhancing amount of the at least one sperm motility enhancing amino acid or amino acid salt. The present vaginal composition may be compounded into a suitable dosage form by procedures that are conventional in the pharmaceutical art, by employing the usual excipients (buffer, emulsifier, preservative, etc.), the choice and amount of which will be apparent to those skilled in the art. As mentioned above, the excipients chosen should not inhibit sperm motility or possess other contraceptive properties.

For example, a pessary may be prepared by mixing the active constituent(s) with at least one polyethylene glycol, the glycol or mixture of glycols having a melting point at or below body temperature. In order to facilitate the efficient dispersion of the active ingredient(s) in the vagina, the pessary may also contain foam producing substances.

Alternatively, in another embodiment of the present invention, a controlled delivery device consists of the active constituent(s) absorbed in a biocompatible, bioinsoluble, flexible, silicone rubber matrix, especially a dimethylpolysiloxane.

A vaginal cream according to this invention may contain a hydrocarbon base (e.g. white petrolatum), a solvent (e.g. glycerin or propylene glycol) and an emulsifier (e.g. cetyl alcohol, stearyl alcohol, sodium lauryl sulphate). A vaginal jelly may contain a solvent (e.g. glycerin or propylene glycol) a gel forming agent (e.g. sodium alginate (especially with calcium ions), tragacanth, gelatin, methyl cellulose, sodium carboxymethylcellulose, carbomer and polyvinyl alcohol) and a nonspermicidal or non-sperm-immobilising preservative. A vaginal foam may contain a fluorinated hydrocarbon propellant and a surfactant or emulsifier.

In order to facilitate the use of the present vaginal pharmaceutical composition there is provided, in a further aspect of the present invention, a method of enhancing sperm motility in the vagina of a female mammal, especially a human female, which comprises applying to the vagina of a female mammal, a sperm motility enhancing amount of at least one sperm motility enhancing amino acid or amino acid salt.

The present vaginal pharmaceutical composition together with evidence of its sperm motility enhancing properties, is illustrated in the following Examples,

MATERIALS AND METHODS

Measurement of Human Sperm Motility

A simple method for measuring human sperm motility was developed as a modification to the method of C. Y. Hong et al., *Br. J. Clin. Pharm.*, 1982, 11, 385. The method used two chambers separated by a membrane and assessed the proportion of spermatozoa, from a small aliquot of semen, that moved across the membrane from the upper to the lower chamber.

MATERIALS a. Nuclepore (Trade Mark) polycarbonate membrane filters (13 mm×5 μm; Sterilin).

b. Silated 10 ml. glass vials.

c. 2 ml Sabre (Trade Mark) disposable plastic syringes. (Philip Harris Medical Ltd.).

d. Phosphate buffered saline (pH 7.3 Dulbecco A (Trade Mark); Oxoid).

e. 10% Formalin solution.

f. Haemocytometers-improved Neubauer (Trade Mark).

g. Semen sample containing immotile sperm, (less than 40% motile), to be used within 4 hours of collection.

METHOD

The apparatus consisted of an upper and a lower chamber, the upper chamber being the plunger of a 2 ml. disposable syringe. A 13 mm diameter Nuclepore membrane filter was bonded to the plunger using dichloromethane.

Aliquots of fresh human semen, taken from subjects having relatively immotile sperm, were mixed, in a 2 to 1 volume ratio, with either phosphate buffered saline (ph 7.3) or a phosphate buffered saline solution of an amino acid(s) (pH 7.3). The mixture was pre-incubated at 37° C. for 30 minutes. After pre-incubation the mixture was vortexed and 100ul was pipetted onto the membrane of the upper chamber. The upper chamber was then inserted into the lower chamber, which contained 1 ml. of phosphate buffered saline at 37° C. The relative positions of the two chambers were fixed so that the fluid levels were equal.

The apparatus was then incubated for 90 min. at 37° C. After this time, the upper chamber was removed and its contents were washed into 0.9 ml phosphate buffered saline containing 50 ul of 10% formalin solution by breaking the membrane. The spermatozoa in the lower chamber were also killed by adding 50 ul of the formalin to the lower chamber.

Finally, the number of spermatozoa in the upper and lower chambers were counted using a haemocytometer. The proportion of spermatozoa that traverse the membrane into the lower chamber is referred to as the trans-membrane migration ratio.

The enhancement of sperm motility achieved by L-arginine, L-aspartic acid, L-histidine, a mixture of L-arginine and L-aspartic acid, arginine aspartate, L-asparagine or L-glutamic acid is given in the Table, as a % of a control experiment (control=100%).

TABLE

Effect of Amino Acids on Sperm Motility (Control = 100%)

| Amino Acid | Concentration (mM) | | | | | |
|---|---|---|---|---|---|---|
| | 0.1 | 1.0 | 5.0 | 10.0 | 25.0 | 50.0 |
| L-Arginine | 107.9 | 119.3 | 130.0 | 118.2 | 119.0 | 96.7 |
| L-Aspartic Acid | 110.5 | 123.9 | 112.5 | 125.5 | 126.8 | — |
| L-Histidine | 111.1 | 129.0 | 122.5 | 124.4 | 136.5 | — |
| L-Arginine and 10 mM L-Aspartic Acid | 110.1 | 118.8 | 127.2 | 139.0 | 126.0 | — |
| L-Arginine and 25 mM L-Aspartic Acid | 109.2 | 109.0 | 106.5 | 126.1 | 130.1 | — |
| Arginine Aspartate | 135.4 | 148.9 | 111.1 | 178.5 | 166.8 | — |
| L-Asparagine | — | 142.5 | 146.6 | 161.1 | 162.7 | — |
| L-Glutamic Acid | — | 124.9 | 122.2 | 108.3 | 15.5 | — |

What we claim is:

1. Method of enhancing sperm motility in the vagina of a human female, which comprises applying into the vagina of the human female a vaginal sperm motility enhancing pharmaceutical composition comprising an effective amount of a sperm motility enhancing agent selected from the group consisting of aspartic acid, glutamic acid, arginine, histidine, asparagine, glutamine and pharmaceuticly acceptable salts thereof, said effective amount being effective only to enhance sperm motility, said sperm motility enhancing agent being distributed in a vaginally acceptable carrier.

2. Method according to claim 1 wherein said sperm motility enhancing agent is arginine or asparagine.

3. Method according to claim 1 wherein said sperm motility enhancing agent is arginine aspartate.

4. Method according to claim 1 wherein the amount of said sperm motility enhancing agent per unit dose is between about 0.02 and 2 mmoles.

5. Method according to claim 4 wherein said unit dose is between about 0.1 and 1 mmole.

6. Method according to claim 1 wherein said sperm motility enhancing agent is an L-amino acid or an L-amino acid salt.

* * * * *